(12) United States Patent
Kim et al.

(10) Patent No.: US 9,839,207 B2
(45) Date of Patent: Dec. 12, 2017

(54) ANIMAL MODEL OF CHARCOT-MARIE-TOOTH DISEASE AS HSP27 MUTANT (S135F) CARRIER

(71) Applicants: Samsung Life Public Welfare Foundation, Seoul (KR); Chong Kun Dang Pharmaceutical Corp, Seoul (KR)

(72) Inventors: Yun Tae Kim, Gyeonggi-do (KR); Byung-Ok Choi, Seoul (KR); Sung Chul Jung, Seoul (KR); Young Bin Hong, Seoul (KR); So-Youn Woo, Seoul (KR); Jin-Mo Park, Seoul (KR)

(73) Assignees: SAMSUNG LIFE PUBLIC WELFARE FOUNDATION, Seoul (KR); CHONG KUN DANG PHARMACEUTICAL CORP, Seoul (KR)

( * ) Notice: Subject to any disclaimer, the term of this patent is extended or adjusted under 35 U.S.C. 154(b) by 0 days.

(21) Appl. No.: 14/873,119

(22) Filed: Oct. 1, 2015

(65) Prior Publication Data
US 2016/0015010 A1 Jan. 21, 2016

Related U.S. Application Data

(63) Continuation of application No. PCT/KR2014/002795, filed on Apr. 1, 2014.

(30) Foreign Application Priority Data

Apr. 2, 2013 (KR) .................. 10-2013-0035740
Apr. 1, 2014 (KR) .................. 10-2014-0038468

(51) Int. Cl.
*A01K 67/027* (2006.01)
*A01K 67/00* (2006.01)
*C12Q 1/68* (2006.01)
*G01N 33/68* (2006.01)
*A61K 49/00* (2006.01)
*C07K 14/47* (2006.01)

(52) U.S. Cl.
CPC ...... *A01K 67/0275* (2013.01); *A61K 49/0008* (2013.01); *C07K 14/4703* (2013.01); *C12Q 1/6883* (2013.01); *G01N 33/6872* (2013.01); *G01N 33/6893* (2013.01); *A01K 2217/052* (2013.01); *A01K 2227/105* (2013.01); *A01K 2267/0306* (2013.01); *C12Q 2600/136* (2013.01); *C12Q 2600/158* (2013.01); *G01N 2333/4703* (2013.01)

(58) Field of Classification Search
USPC ............................................ 800/18, 3, 8, 21
See application file for complete search history.

(56) References Cited

U.S. PATENT DOCUMENTS

| 4,873,191 | A * | 10/1989 | Wagner | .................... A01H 1/00 435/317.1 |
|---|---|---|---|---|
| 9,238,028 | B2 * | 1/2016 | Van Den Bosch | .. A61K 31/422 |
| 9,267,140 | B2 * | 2/2016 | Baltimore | .......... C12N 15/1132 |
| 2014/0329849 | A1 * | 11/2014 | Van Den Bosch | .. A61K 31/422 514/292 |

FOREIGN PATENT DOCUMENTS

| KR | 10-2005-0096347 A | 10/2005 |
|---|---|---|
| KR | 10-2013-0027596 A | 3/2013 |
| WO | WO 2012-045804 A1 | 4/2012 |

OTHER PUBLICATIONS

Swarthout et al., Zinc Finger Nucleases: A new era for transgenic animals Annals of Neurosciences, vol. 18, No. 1 (2011) Abstract.*
Swanson et al Anesth Analg. Oct. 1992;75(4):549-54.Fertilization and mouse embryo development in the presence of midazolam.*
Dunn et al Transgenic animals and their impact on the drug discovery industry DDT o vol. 10, No. 11 o Jun. 2005 Reviews pp. 757-767.*
Kim et al ., Transcriptome analysis of human gastric cancer Journal Mamm. Genome 16 (12), 942-954 (2005).*
d'Ydewalle et al., "HDAC6 inhibitors reverse axonal loss in a mouse model of mutant HSPB1-induced Charcot-Marie-Tooth disease," *Nature Medicine* 17(8):968-974 (Aug. 2011).
International Search Report from parent PCT Application No. PCT/KR2014/002795, 2 pages (dated Jul. 25, 2014).
Sereda et al., "A transgenic rat model of charcot-marie-tooth disease," *Neuron* 16:1049-1060 (May 1996).

* cited by examiner

*Primary Examiner* — Maria Leavitt
(74) *Attorney, Agent, or Firm* — Klarquist Sparkman, LLP

(57) ABSTRACT

The present invention relates to a HSP27 mutation (S135F) mediated Charcot-Marie-Tooth disease (CMT) animal model. Particularly, the vector expressing mutant HSP27 protein wherein the 135$^{th}$ serine is substituted with phenylalanine has been injected in the mouse zygote and then the mouse harboring the expression vector was selected. The selected mouse was confirmed to display Charcot-Marie-Tooth disease phenotype, so that the animal model was expected to be efficiently used for the evaluation of the effect of Charcot-Marie-Tooth disease treating material candidates.

3 Claims, 8 Drawing Sheets

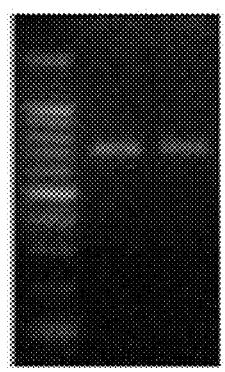
FIG. 1A
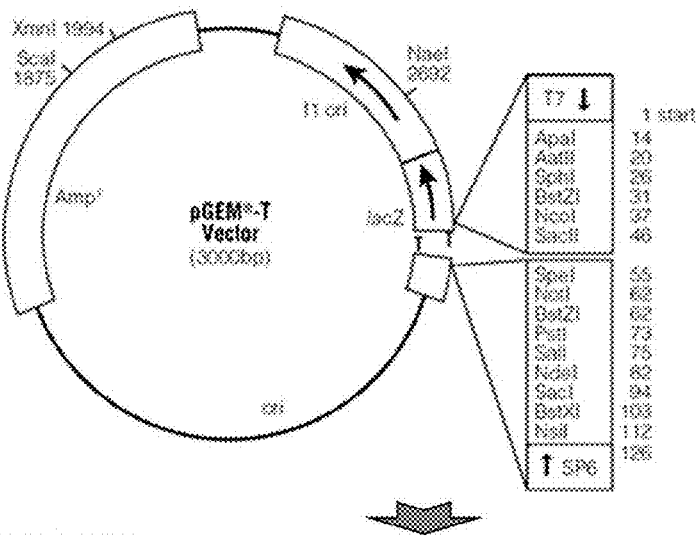
FIG. 1B
FIG. 1C
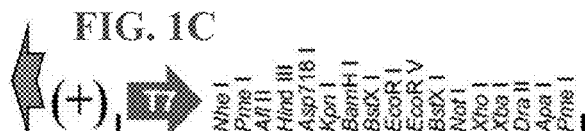
FIG. 1D
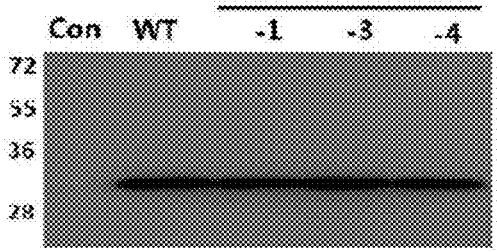
FIG. 1E

SEQUENCE LISTING

```
<160> NUMBER OF SEQ ID NOS: 5

<210> SEQ ID NO 1
<211> LENGTH: 655
<212> TYPE: DNA
<213> ORGANISM: Homo sapiens

<400> SEQUENCE: 1
tttctgagca gacgtccaga gcagagtcag ccagcatgac cgagcgccgc gtcccttct      60 cgctcctgcg gggccccagc tgggaccct tccgcgactg gtacccgcat agccgcctct    120
tcgaccaggc cttcggggtg ccccggctgc cggaggagtg gtcgcagtgg ttaggcggca    180
gcagctggcc aggctacgtg cgcccctgc ccccgccgc catcgagagc cccgcagtgg    240
```

```
ccgcgcccgc ctacagccgc gcgctcagcc ggcaactcag cagcggggtc tcggagatcc    300
ggcacactgc ggaccgctgg cgcgtgtccc tggatgtcaa ccacttcgcc ccggacgagc    360
tgacggtcaa gaccaaggat ggcgtggtgg agatcaccgg caagcacgag gagcggcagg    420
acgagcatgg ctacatcttc cggtgcttca cgcggaaata cacgctgccc cccggtgtgg    480
accccaccca gtttcctcc tccctgtccc ctgagggcac actgaccgtg gaggccccca    540
tgcccaagct agccacgcag tccaacgaga tcaccatccc agtcaccttc gagtcgcggg    600
cccagcttgg gggcccagaa gctgcaaaat ccgatgagac tgccgccaag taaag        655

<210> SEQ ID NO 2
<211> LENGTH: 25
<212> TYPE: DNA
<213> ORGANISM: Artificial Sequence
<220> FEATURE:
<223> OTHER INFORMATION: Primer

<400> SEQUENCE: 2
atgaccgagc gccgcgtccc cttct                                          25

<210> SEQ ID NO 3
<211> LENGTH: 23
<212> TYPE: DNA
<213> ORGANISM: Artificial Sequence
<220> FEATURE:
<223> OTHER INFORMATION: Primer

<400> SEQUENCE: 3
ttacttggcg gcagtctcat cgg                                            23

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
gacgtcaatg ggagtttgtt tt                                             22

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
gagatgtagc catgctcgtc ct                                             22
```

ANIMAL MODEL OF CHARCOT-MARIE-TOOTH DISEASE AS HSP27 MUTANT (S135F) CARRIER

CROSS REFERENCE TO RELATED APPLICATIONS

This is a continuation of PCT Application No. PCT/KR2014/002795, filed on Apr. 1, 2014, which is incorporated by reference, and which claims priority to Korean Application No. 10-2014-0038468, filed on Apr. 1, 2014 and Korean Application No. 10-2013-0035740, filed on Apr. 2, 2013.

BACKGROUND OF THE INVENTION

1. Field of the Invention

The present invention relates to a HSP27 mutation (S135F) mediated Charcot-Marie-Tooth disease animal model.

2. Description of the Related Art

The experiment using an animal model is unavoidable and has to be done before treating human in the study targeting human for the development of a new drug and a novel treatment method. However, considering how big is the number of human diseases, the number of animal models that can copy such human disease is very small, which has been a big barrier for the development of a new drug and a novel technique for disease treatment. A variety of animal models can be constructed with different characteristics and effects according to the purpose of use. The methods to construct disease animal models known so far can be divided into three groups. First, it is the method to use a natural mutant form as an animal disease model; the second is the experimental method to induce disease by administering a chemical or transplanting a manipulated cell line; and the most recent method is the transfection via gene transplantation developed fast from the molecular genetical approach. For the study to develop a new drug and a novel treatment method, it is very important to establish an efficient animal model construction system based on various different approaching methods for securing animal models and co-operation of them.

Hereditary peripheral neuropathy is largely divided into three categories: which are hereditary motor and sensory neuropathy (HMSN), hereditary motor neuropathy (HMN), and hereditary sensory neuropathy (HSN). Among them, hereditary motor and sensory neuropathy occupies the majority of the patients and is also well known as Charcot-Marie-Tooth disease (CMT). Charcot-Marie-Tooth disease was first identified by French scientists Charcot and Marie and English Tooth in 1886. Since then, the disease has been called as CMT after the first letters of their names. Charcot-Marie-Tooth disease is the general name for all the genetic disease with defect in motor neurons and sensory neurons, and has the highest incidence rate (1/2500 people) among rare diseases. In the past, this disease was understood rather simply as the disease caused by muscle atrophy in the distal lower leg. Patients with this disease have legs in the shape of a champagne bottle standing up side down because of the muscle atrophy. However, this disease is now recognized as a syndrome rather than a single disease. There has been new additions recently to CMT pathogenesis, which is a big help not only for the pathophysiological study but also for the classification of complicated clinical types and genotypes.

Over the past research years, at least 40 genetic loci for hereditary motor and sensory neuropathy have been identified by gene cloning technique and at least 20 causing genes have also been identified. However, many of hereditary motor and sensory neuropathy patients have still be confirmed not to be associated with the above identified loci, suggesting that there would be at least 50 more causing genes of HMSN. So, the constituents that form various different nervous tissues have been identified. Likewise, it is expected that there might be a variety of types of hereditary neuropathies as there are a variety of hereditary muscular dystrophies. As a potential reasonable drug therapy for CMT1A, the most frequent type of HMSN, onapriston, ascorbic acid, and NT-3 (neurotrophin-3) have been drawing our attention in relation to diagnosis and treatment as well.

Heat shock protein (HSP) is well known as molecular chaperone and anti-apoptotic protein, which is expressed in most cells and well preserved therein. Heat shock proteins are divided into five groups according to the amino acid sequence and molecular weight, which are 100~110 kDa family, 83~90 kDa family, 66~78 kDa family, 60 kDa family, and 15~30 kDa family. HSP27 belongs to the small heat shock protein family and is expressed in mammal tissues including muscle and nervous tissue. HSP27 is widely distributed in motor neurons and sensory neurons.

HSP27 is the low molecular protein that is functioning in many ways in cells. This protein forms a colony itself for self-defense against external environmental stimuli such as free radicals or toxins.

SUMMARY OF THE INVENTION

It is an object of the present invention to provide a HSP27 mutation (S135F) mediated Charcot-Marie-Tooth disease animal model, a preparation method thereof, and a screening method of Charcot-Marie-Tooth disease treating drug candidates using the same.

To achieve the above object, the present invention provides a zygote of the Charcot-Marie-Tooth disease (CMT) mouse model introduced with the expression vector expressing the mutant HSP27 protein wherein serine, the $135^{th}$ amino acid from N-terminal, has been replaced with phenylalanine.

The present invention also provides a transgenic mouse obtained by implanting the zygote of the invention in the uterus of a surrogate mother.

The present invention further provides a method for preparing a Charcot-Marie-Tooth disease mouse model comprising the following steps:

1) constructing an expression vector that can express the mutant HSP27 protein wherein serine, the $135^{th}$ amino acid from N-terminal, has been replaced with phenylalanine;

2) introducing the expression vector expressing the mutant HSP27 of step 1) in a zygote of a mouse; and 3) obtaining a transgenic mouse by implanting the zygote prepared in step 2) in the uterus of a surrogate mother.

In addition, the present invention provides a screening method of Charcot-Marie-Tooth disease preventive and therapeutic material candidates comprising the following steps:

1) administering the samples to the transgenic mouse of the invention;

2) measuring the expression level of the mutant HSP27 gene or protein in the transgenic mouse treated with the sample of step 1); and 3) selecting the sample that could significantly reduce the expression of the mutant HSP27 gene or protein, compared with the control group not-treated with the sample.

Advantageous Effect

The present invention relates to a HSP27 mutation (S135F) mediated Charcot-Marie-Tooth disease (CMT) animal model. Particularly, the vector expressing mutant HSP27 protein wherein the 135$^{th}$ serine is substituted with phenylalanine has been injected in the mouse zygote and then the mouse harboring the expression vector was selected. The selected mouse was confirmed to display Charcot-Marie-Tooth disease phenotype, so that the animal model was expected to be efficiently used for the screening of precursors for the development of a CMT treating drug.

The present inventors tried to develop a disease-tailored medical technology for Charcot-Marie-Tooth disease. As a result, the inventors separated fibroblasts from CMT patient derived samples, from which the expression vector expressing the mutant HSP27 (S135F) protein wherein the 135$^{th}$ serine had been replaced with phenylalanine was constructed. After injecting the expression vector into a zygote, the inventors implanted the zygote in a surrogate mother. Then, the mouse harboring the expression vector in genomic DNA was selected. As a result, the Charcot-Marie-Tooth disease phenotype was confirmed in the mouse harboring the expression vector expressing the mutant HSP27 (S135F) protein. The present inventors, thereafter, conformed that the Charcot-Mari-Tooth disease animal model could be efficiently used for the screening of precursors for the development of a CMT treating drug, leading to the completion of this invention.

BRIEF DESCRIPTION OF THE DRAWINGS

The application of the preferred embodiments of the present invention is best understood with reference to the accompanying drawings, wherein:

FIGS. 1A-1E are digital images and diagrams illustrating the method for preparing the expression vector expressing the mutant HSP27 (S135F) protein.

A: amplifying HSP27 protein in CMT patient sample by PCR,

B: cloning the amplified HSP27 protein in pGEM-T vector,

C: cloning the HSP27 protein cloned in pGEM-T vector in pcDNA3.1(+),

D: confirming S135F mutation in the mutant HSP27 protein inserted in the expression vector; and E: confirming the expression of HSP27 (S135F) protein (−1: clone 1, −3: clone 3, −4: clone 4).

Figure 2:
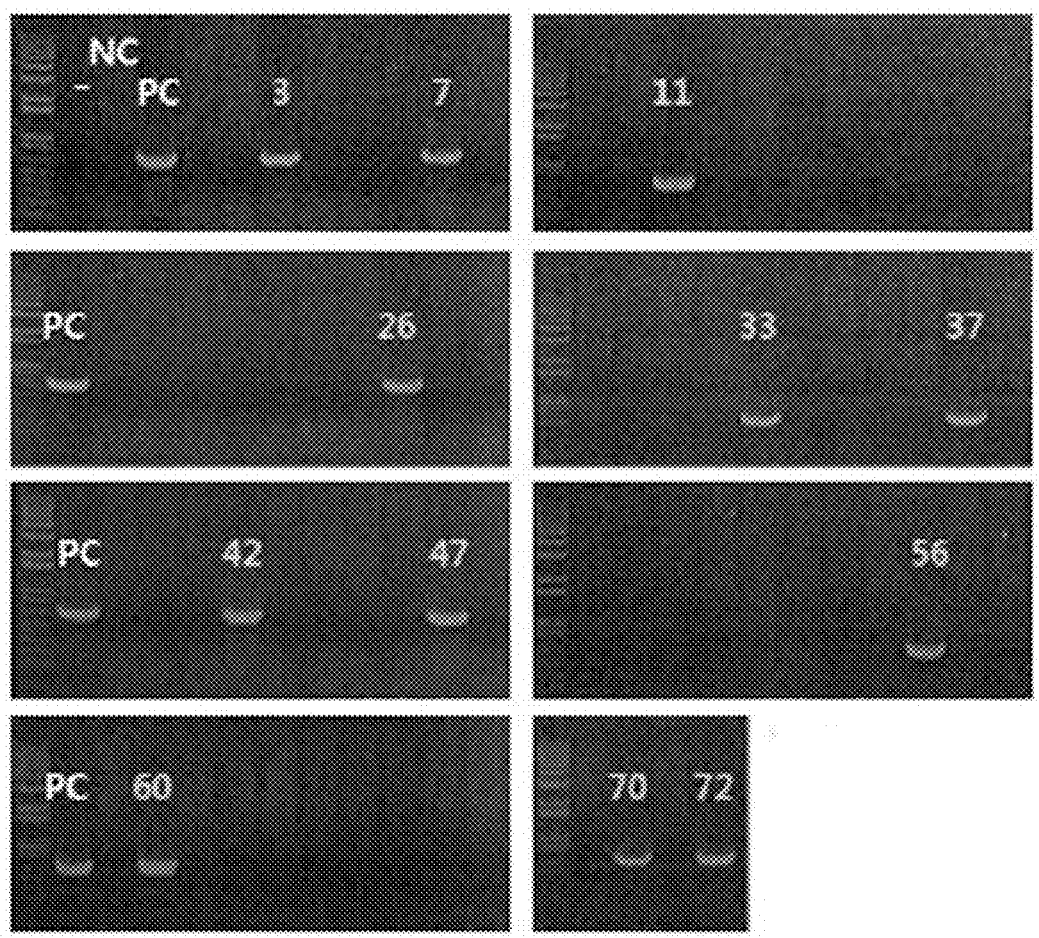

FIG. 2 is a digital image illustrating the selection of the mouse harboring the HSP27 (S135F) expression vector. Precisely, the mouse developed from the zygote introduced with the HSP27 (S135F) expression vector was investigated and if the expression vector was confirmed in its genomic DNA, the mouse was selected.

Figure 3:
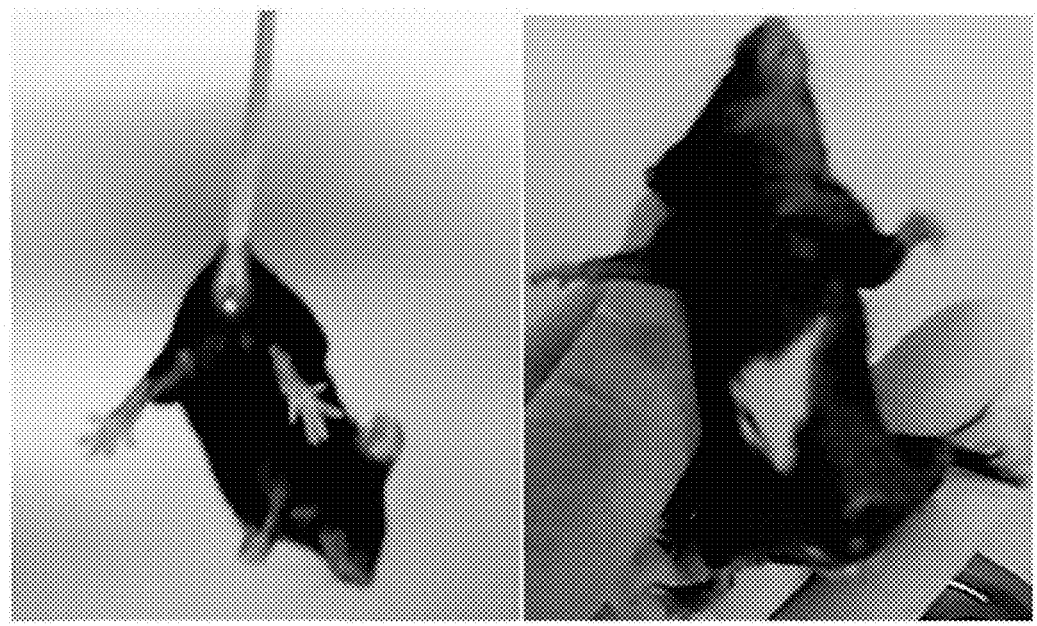

FIG. 3 is a digital image illustrating the mouse expressing HSP27 (S135F) protein.

Figure 4:
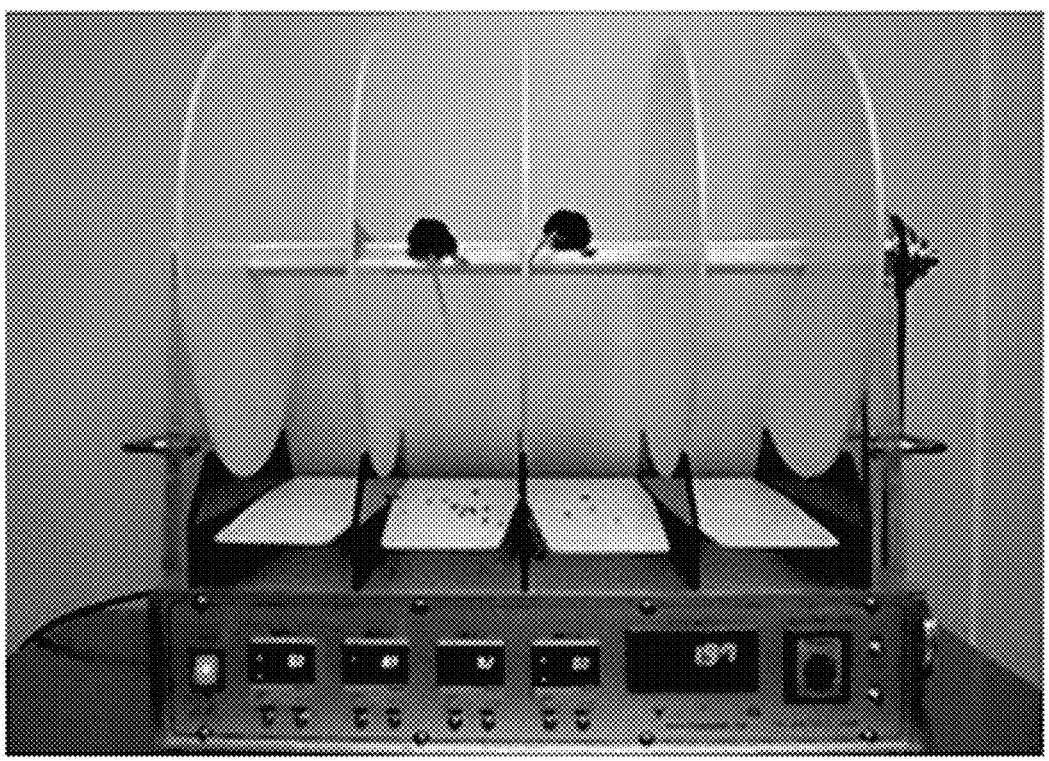

FIG. 4 is a digital image illustrating the process of rotarod test.

Figure 5:
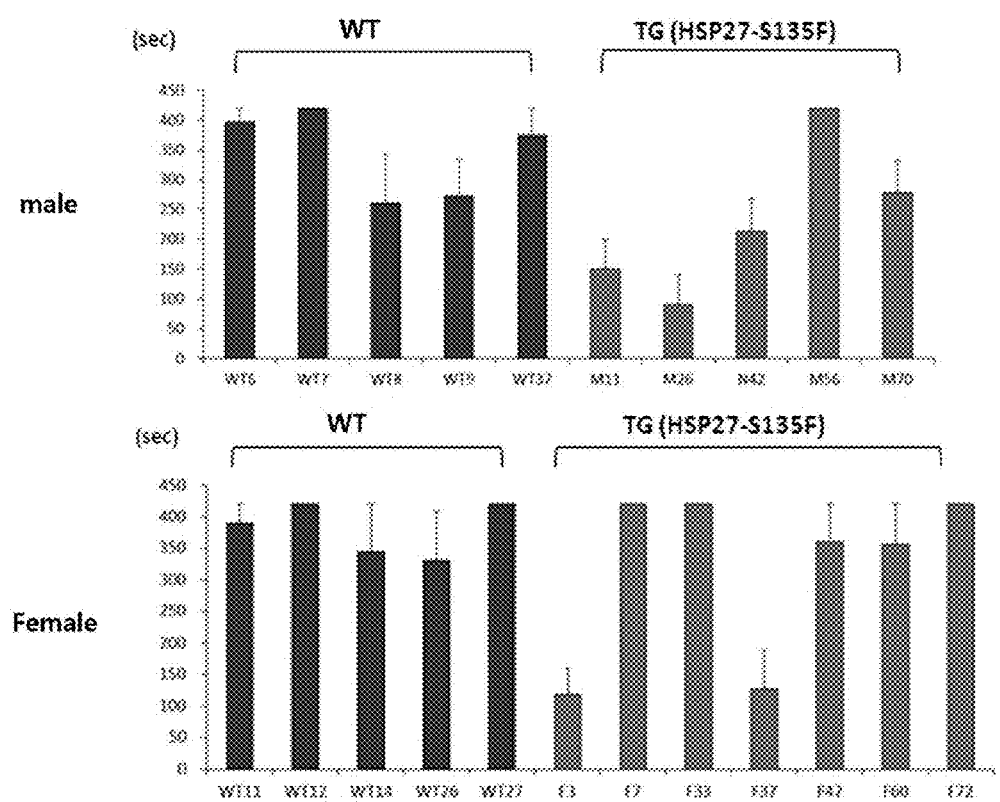

FIG. 5 is a set of bar graphs illustrating the evaluation of lower limb strength of the first generation mouse (both male and female) via rotarod test.

Figure 6:
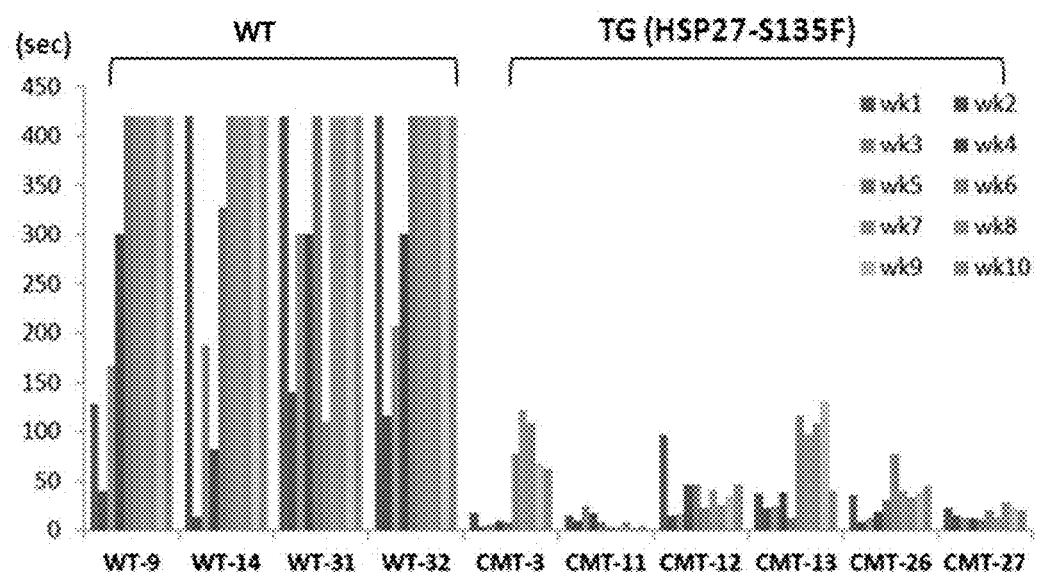

FIG. 6 is a set of bar graphs illustrating the evaluation of lower limb strength of the baby of the first generation mouse via rotarod test.

Figure 7:
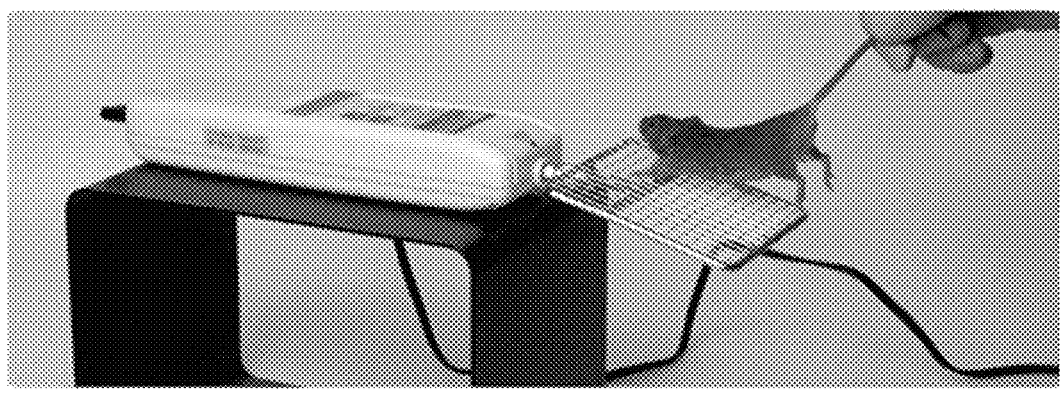

FIG. 7 is a digital image illustrating the process of grip strength test.

Figure 8:
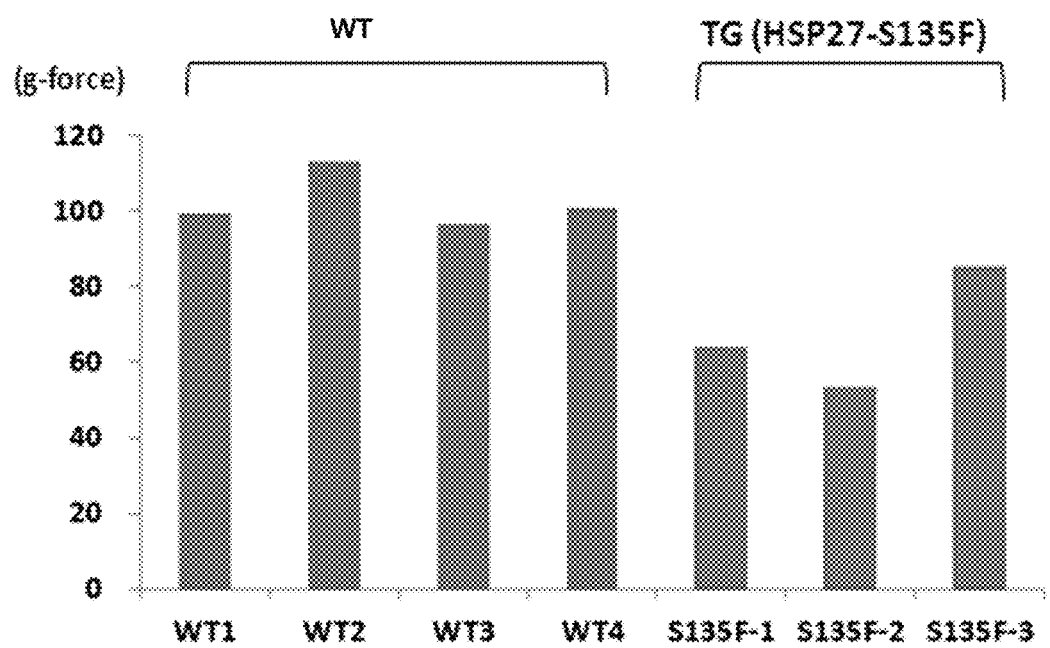

FIG. 8 is a bar graph illustrating the evaluation of lower limb strength of the baby of the first generation mouse selected in this invention via grip strength test.

SEQUENCE LISTING

The Sequence Listing is submitted as an ASCII text file [7037-95836-01_Sequence_Listing.txt, Sep. 29, 2015, 2.16 KB], which is incorporated by reference herein.

DESCRIPTION OF THE PREFERRED EMBODIMENTS

Hereinafter, the present invention is described in detail.

The present invention provides a zygote of the Charcot-Marie-Tooth disease (CMT) mouse model introduced with the expression vector expressing the mutant HSP27 protein wherein serine, the 135$^{th}$ amino acid from N-terminal, has been replaced with phenylalanine.

The mutant HSP27 protein wherein serine, the 135th amino acid from N-terminal,' has been replaced with phenylalanine preferably comprises the amino acid sequence represented by SEQ ID NO: 1, but not always limited thereto. To obtain the said mutant, the codon TCC that encodes serine in HSP27 gene is preferably replaced with the codon TTC or TTT that encodes phenylalanine. In a preferred embodiment of the present invention, it is more preferably replaced with TTC, but not always limited thereto.

The present invention also provides a transgenic mouse obtained by implanting the zygote of the invention in the uterus of a surrogate mother.

The said transgenic mouse is obtained by implanting the zygote of the invention in the uterus of a surrogate mother, which expresses the mutant HSP27 wherein serine, the 135$^{th}$ amino acid from N-terminal, has been replaced with phenylalanine, and this mouse model preferably has Charcot-Marie-Tooth disease induced, but not always limited thereto. The transgenic mouse of the invention can be constructed by the conventional transgenic mouse preparation method.

In a preferred embodiment of the present invention, the inventors obtained HSP27 mRNA from the CMT patient sample. The obtained HSP27 mRNA was amplified by PCR to prepare S135F mutant (see FIG. 1A). The amplified HSP27 (S135F) protein was cloned in an expression vector (see FIG. 1C), which proceeded to DNA sequencing. As a result it was confirmed that the 135$^{th}$ amino acid serine was replaced with phenylalanine (see FIG. 1D). The said HSP27 (S135F) expression vector was introduced into a cell line for transfection, followed by investigation of the expression of HSP protein (see FIG. 1E).

The constructed HSP27 (S135F) expression vector was injected in a zygote of a mouse, which was transplanted in the uterus of a surrogate mother. The mouse that confirmed the expression of the HSP27 (S135F) expression vector was selected (see FIG. 2). Then, rotarod test and grip strength test were performed. As a result, it was confirmed that the constructed HSP27 (S135F) mutant mouse showed significantly reduced lower limb strength, compared with the wild-type control group (see FIGS. 5, 6, and 8), suggesting that the phenotype of Charcot-Marie-Tooth disease was confirmed therein.

Therefore, it was confirmed that the HSP27 (S135F) mediated CMT animal model of the present invention can be efficiently used for the screening of a preventive and therapeutic agent for Charcot-Marie-Tooth disease.

The present invention further provides a method for the preparation of a Charcot-Marie-Tooth disease mouse model comprising the following steps:

1) constructing an expression vector that can express the mutant HSP27 protein wherein serine, the 135$^{th}$ amino acid from N-terminal, has been replaced with phenylalanine;

2) introducing the expression vector expressing the mutant HSP27 of step 1) in a zygote of a mouse; and 3) obtaining a transgenic mouse by implanting the zygote prepared in step 2) in the uterus of a surrogate mother.

The mutant HSP27 protein wherein serine, the 135$^{th}$ amino acid from N-terminal, has been replaced with phenylalanine of step 1) preferably comprises the amino acid sequence represented by SEQ ID NO: 1, but not always limited thereto. To obtain the said mutant, the codon TCC that encodes serine in HSP27 gene is preferably replaced with the codon TTC or TTT that encodes phenylalanine. In a preferred embodiment of the present invention, it is more preferably replaced with TTC, but not always limited thereto.

The expression vector herein preferably contains a CMV promoter, and is preferably a mammalian expression vector, but not always limited thereto.

In a preferred embodiment of the present invention, the inventors confirmed that the HSP27 (S135F) mediated Charcot-Marie-Tooth disease animal model of the present invention could be efficiently used for the screening of a preventive and therapeutic agent for Charcot-Marie-Tooth disease.

In addition, the present invention provides a screening method of Charcot-Marie-Tooth disease preventive and therapeutic material candidates comprising the following steps:

1) administering the samples to the transgenic mouse of the invention;

2) measuring the expression level of the mutant HSP27 gene or protein in the transgenic mouse treated with the sample of step 1); and 3) selecting the sample that could significantly reduce the expression of the mutant HSP27 gene or protein, compared with the control group not-treated with the sample.

The sample of step 1) is preferably selected from the group consisting of peptide, protein, non-peptide compound, active compound, fermented product, cell extract, plant extract, animal tissue extract, and blood plasma, but not always limited thereto.

The transgenic mouse of step 1) is obtained by implanting the zygote of the invention in the uterus of a surrogate mother, which expresses the mutant HSP27 wherein serine, the 135$^{th}$ amino acid from N-terminal, has been replaced with phenylalanine, and this mouse model preferably has Charcot-Marie-Tooth disease induced, but not always limited thereto. The transgenic mouse of the invention can be constructed by the conventional transgenic mouse preparation method.

In step 2), the gene expression level is preferably measured by the method selected from the group consisting of RT-PCR, real-time RT-PCR, microarray, northern blotting, SAGE (serial analysis of gene expression), and RNase protection assay, but not always limited thereto. The protein expression level is preferably measured by the method selected from the group consisting of western blotting, enzyme-linked immunosorbent assay (ELISA), immunohistochemical staining, immunoprecipitation, and immunofluorescence, but not always limited thereto.

In a preferred embodiment of the present invention, the inventors confirmed that the HSP27 (S135F) mediated Charcot-Marie-Tooth disease animal model of the present invention could be efficiently used for the screening of a preventive and therapeutic agent for Charcot-Marie-Tooth disease.

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Construction of HSP27 (S135F) Expression Vector

<1-1> Construction of the expression vector expressing the S135F mutant form of HSP27 protein The expression vector expressing the mutant HSP27 protein that could cause Charcot-Marie-Tooth disease was constructed.

Particularly, mRNA was extracted from the fibroblasts obtained from CMT patient by using RNeasy minikit (QIAGEN, Germany) according to the manufacturer's instruction, from which cDNA was synthesized by using Superscript reverse transcriptase kit (Invitrogen, USA). PCR was performed with the synthesized cDNA as a template by using the below primers (94° C. for 30 seconds, 60° C. for 30 seconds, 72° C. for 30 seconds, 35 cycles) (FIG. 1A). The PCR product was cloned in pGEM-T Easy vector (Promega, USA) (FIG. 1B).

```
Forward (SEQ ID NO: 2):
5'-atgaccgagcgccgcgtccccttct-3',
and

Reverse (SEQ ID NO: 3):
5'-ttacttggcggcagtctcatcgg-3'.
```

The sequence of the S135F mutant form of HSP27 gene was confirmed, followed by cloning in pcDNA3.1(+) (Invitrogen, USA) (FIG. 1C) containing CMV promoter by using the restriction enzyme EcoRI, resulting in the construction of pcDNA3.1(+) HSP27 (S135F) expression vector.

As a result, as shown in FIG. 1D, it was confirmed that serine (S), the 135$^{th}$ amino acid of HSP27, has been replaced with phenylalanine (F) (FIG. 1D).

<1-2> Expression of HSP27 (S135F) Protein

Western blotting was performed to confirm the expression of the HSP27 (S135F) constructed by the method of Example <1-1>.

Particularly, HEK293 cell line (ATCC) was transfected with the HSP27 (S135F) expression vector [pcDNA3.1(+) HSP27 (S135F)] constructed in Example <1-1>. 24 hours later, the cells were washed with PBS, followed by lysis using 1×RIPA. The extracted protein was quantified by BCA method. The equal amount of protein was separated by electrophoresis, which was transferred on nitrocellulose membrane (Amersham Biosciences, Great Britain). To prevent non-specific binding of protein, 5% fat-free milk was added to PBS containing 0.1% Tween 20. The membrane was treated with anti-HSP27 antibody (Santa Cruz Biotechnology, USA) as the primary antibody, followed by reaction at 4° C. for overnight. Then, the cells were washed three times at 5 minutes intervals. The secondary antibody [anti-goat IgG-HRP (anti-goat IgG-HRP), Santa Cruz, USA] was treated thereto, followed by reaction for 1 hour. The membrane was developed by ECL method (Pierce, Rockford, Ill., USA).

As a result, as shown in FIG. 1E, it was confirmed that HSP27 (S135F) protein was significantly expressed in HEK293 cell line (FIG. 1E).

EXAMPLE 2

Construction of Mouse Model

The mouse model was constructed by using the pcDNA3.1(+) HSP27 expression vector expressing HSP27 (A135F) prepared by the method of Example 1 and C57BL/6NCrliOri mouse (OrientBio, Korea).

Particularly, in order to prepare a zygote, a female mouse was injected with PMSG and hCG hormone at 48 hours intervals to induce super-ovulation, followed by mating with a male mouse. Next day morning, vaginal plug was checked to confirm the success of mating. The zygote was obtained from the female mouse oviduct which was confirmed to have vaginal plug. The expression vector expressing HSP27 (S135F) was injected through zona pellucida and cytoplasm into the zygote by using a micro pipette under microscope. Among the zygotes injected with DNA, those who survived were selected and transplanted in the oviduct of a surrogate mother. 19 days after the transplantation, total 72 mice were obtained from normal delivery. PCR was performed (94° C. for 30 seconds, 60° C. for 30 seconds, 72° C. for 30 seconds, 35 cycles) by using the below primers. As a result, the mice confirmed to have the HSP27 (S135F) expression vector in their genomic DNA were selected.

```
Forward2 (SEQ ID NO: 4):
5'-gacgtcaatgggagtttgtttt-3',
and

Reverse2 (SEQ ID NO: 5):
5'-gagatgtagccatgctcgtcct-3'.
```

As shown in FIG. 2, 12 mice expressing HSP27 (S135F) were selected (FIG. 2) and confirmed to have Charcot-Marie-Tooth disease.

EXPERIMENTAL EXAMPLE 1

Confirmation of CMT Phenotype by Behavioral Evaluation of the Mouse Expressing HSP27

<1-1> Measurement of Lower Limb Strength of Mouse via Rotarod Test

To confirm whether or not the mouse prepared in Example 2 had the phenotype of Charcot-Marie-Tooth disease, rotarod test, the behavioral assessment test, was performed (FIG. 4).

Particularly, the mouse was located on rotarod that is moving at the speed of 2 m/s. The time for the mouse to sustain itself on the rotarod was measured. Before the test, the mouse was allowed to practice three times for a week for adaptation. On the day of recording, 1 minute-practice was allowed before the test. The endurance time was measured once a week. The time recording was continued up to 7 minutes. The time less than 7 minutes was recorded as it was, and if the endurance time was less than 3 minutes, total 3 attempts were allowed and the best record was recorded.

As a result, as shown in FIG. 5, total twelve first generation mice were selected for the test and they were separated by gender, and the test began when they were 5 month old and continued for 3 months, once a week. The recorded times were averaged. Among them, M11 and M26 displayed the same phenotype of CMT as the one observed in CMT patient (FIG. 5).

Lower limb strength was measured via rotarod test for 10 weeks, once a week, with the babies of the selected first generation M11 and M26 mice. As a result, as shown in FIG. 6, lower limb strength of them was significantly decreased, compared with the wild-type mice (FIG. 6).

<1-2> Measurement of Muscular Strength of the Mouse via Grip Strength Test

To confirm whether or not the babies of the selected M11 and M26 of Experimental Example <1-1> had the phenotype of Charcot-Marie-Tooth disease, grip strength test, one of the behavioral assessment tests, was performed (FIG. 7).

Particularly, the instant grip strength of the test mice with four-feet on the net attached on the grip tester machine was sensed by the measuring instrument and the result was presented as g-force unit. Three practice sessions were given before the measurement, and on the day of the test, test was performed in triplicate and the mean value was recorded.

As a result, as shown in FIG. 8, lower limb strength of the HSP27-S135F mutant mouse was significantly decreased, compared with the wild-type mouse (FIG. 8). This result was consistent with that of the rotarod test in Experimental Example <1-1>.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A transgenic mouse whose genome comprises a transgene, said transgene comprising a cytomegalovirus (CMV) promoter operably linked to a nucleic acid sequence encoding a mutant heat shock protein (HSP)27, wherein the mutant HSP27 comprises the amino acid sequence encoded by the nucleic acid sequence of SEQ ID NO: 1, wherein expression of the transgene results in a transgenic mouse exhibiting a phenotype of a Charcot-Marie-Tooth disease characterized by impaired lower limb strength at one week of age as compared to a wild-type mouse.

2. A method of producing the transgenic mouse of claim 1, the method comprising:

a) constructing a transgene comprising a CMV promoter operably linked to a nucleic acid sequence encoding a mutant HSP27, wherein the mutant HSP27 comprises the amino acid sequence encoded by the nucleic acid sequence of SEQ ID NO:1;

b) introducing the transgene of step a) in a zygote of a mouse;

c) transferring the zygote comprising the transgene of a) in the uterus of a surrogate mother; and d) allowing the transferred zygote comprising the transgene of a) to develop to produce a transgenic mouse whose genome comprises a transgene comprising CMV promoter operably linked to a nucleic acid sequence encoding a mutant HSP27, wherein the mutant HSP27 comprises an amino acid sequence encoded by the nucleic acid sequence of SEQ ID NO: 1, wherein expression of the transgene results in a transgenic mouse exhibiting a phenotype of a Charcot-Marie-Tooth disease characterized by impaired limb strength at one week of age as compared to a wild-type mouse.

3. A method for screening a drug for the potential of treating Charcot-arie-Tooth disease, comprising administering a drug to the transgenic mouse of claim 1, and comparing the results obtained for impaired lower limb strength with treated mice versus untreated mice, less impaired limb strength being indicative for a therapeutic potential.

* * * * *